(12) United States Patent
Franke

(10) Patent No.: US 11,944,787 B2
(45) Date of Patent: Apr. 2, 2024

(54) INJECTOR DEVICE

(71) Applicant: SANOFI, Paris (FR)

(72) Inventor: Beate Franke, Frankfurt am Main (DE)

(73) Assignee: Sanofi, Paris (FR)

(*) Notice: Subject to any disclaimer, the term of this patent is extended or adjusted under 35 U.S.C. 154(b) by 762 days.

(21) Appl. No.: 16/759,675

(22) PCT Filed: Oct. 29, 2018

(86) PCT No.: PCT/EP2018/079548
§ 371 (c)(1),
(2) Date: Apr. 27, 2020

(87) PCT Pub. No.: WO2019/086371
PCT Pub. Date: May 9, 2019

(65) Prior Publication Data
US 2020/0289755 A1 Sep. 17, 2020

(30) Foreign Application Priority Data

Oct. 30, 2017 (EP) .................... 17306487

(51) Int. Cl.
*A61M 5/20* (2006.01)
*A61M 5/32* (2006.01)

(52) U.S. Cl.
CPC ........ *A61M 5/2033* (2013.01); *A61M 5/3202* (2013.01); *A61M 2005/2013* (2013.01);
(Continued)

(58) Field of Classification Search
CPC .............. A61M 5/2033; A61M 5/3271; A61M 5/3275; A61M 2005/2013;
(Continued)

(56) References Cited

U.S. PATENT DOCUMENTS 4,840,185 A * 6/1989 Hernandez .......... A61M 5/3271
600/583
2008/0147006 A1 6/2008 Brunnberg et al.
(Continued)

FOREIGN PATENT DOCUMENTS

CN 102917738 2/2013
CN 102917742 2/2013
(Continued)

OTHER PUBLICATIONS

PCT International Preliminary Report on Patentability in Application No. PCT/EP2018/079548, dated May 5, 2020, 8 pages.
(Continued)

*Primary Examiner* — James D Ponton
*Assistant Examiner* — Neeraja Gollamudi
(74) *Attorney, Agent, or Firm* — Fish & Richardson P.C.

(57) ABSTRACT

An injector device includes an elongate housing configured to receive container of medicament. The injector device also includes a needle sleeve mounted within the housing and moveable between an extended position in which the needle sleeve at least partially extends from the distal end of the housing, and a retracted position in which the needle sleeve is received further within the housing than in the extended position. The injector device also includes a release mechanism configured to control actuation of a piston rod. The release mechanism includes a rotatable member disposed within the housing and in cooperating engagement with the needle sleeve such that movement of the needle sleeve from the extended position to the retracted position causes the rotatable member to rotate within the housing from a first position to a second position.

21 Claims, 6 Drawing Sheets

(52) U.S. Cl.
CPC . *A61M 2005/202* (2013.01); *A61M 2005/206* (2013.01); *A61M 2005/2073* (2013.01); *A61M 2005/2086* (2013.01)

(58) Field of Classification Search
CPC ...... A61M 2005/202; A61M 2005/206; A61M 2005/2086
See application file for complete search history.

(56) References Cited

U.S. PATENT DOCUMENTS

| | | | |
|---|---|---|---|
| 2013/0324934 A1* | 12/2013 | Holmqvist | A61M 5/2033 604/192 |
| 2018/0161523 A1* | 6/2018 | Sanders | A61M 5/326 |

FOREIGN PATENT DOCUMENTS

| | | | |
|---|---|---|---|
| CN | 104968381 | 10/2015 | |
| EP | 1932558 | 6/2008 | |
| EP | 2583708 | 4/2013 | |
| EP | 2944341 | 11/2015 | |
| JP | 2008-212631 | 9/2008 | |
| JP | 2016-500321 | 1/2016 | |
| JP | 2016-537080 | 12/2016 | |
| RU | 2014113407 | 10/2015 | |
| WO | WO 2011/111006 | 9/2011 | |
| WO | WO 2011/123024 | 10/2011 | |
| WO | WO 2013/034984 | 3/2013 | |
| WO | WO 2014/095424 | 6/2014 | |
| WO | WO-2014095424 A1 * | 6/2014 | .......... A61M 5/2033 |
| WO | WO 2015/073740 | 5/2015 | |
| WO | WO 2016/193349 | 12/2016 | |

OTHER PUBLICATIONS

PCT International Search Report and Written Opinion in Application No. PCT/EP2018/079548, dated Dec. 11, 2018, 13 pages.

* cited by examiner

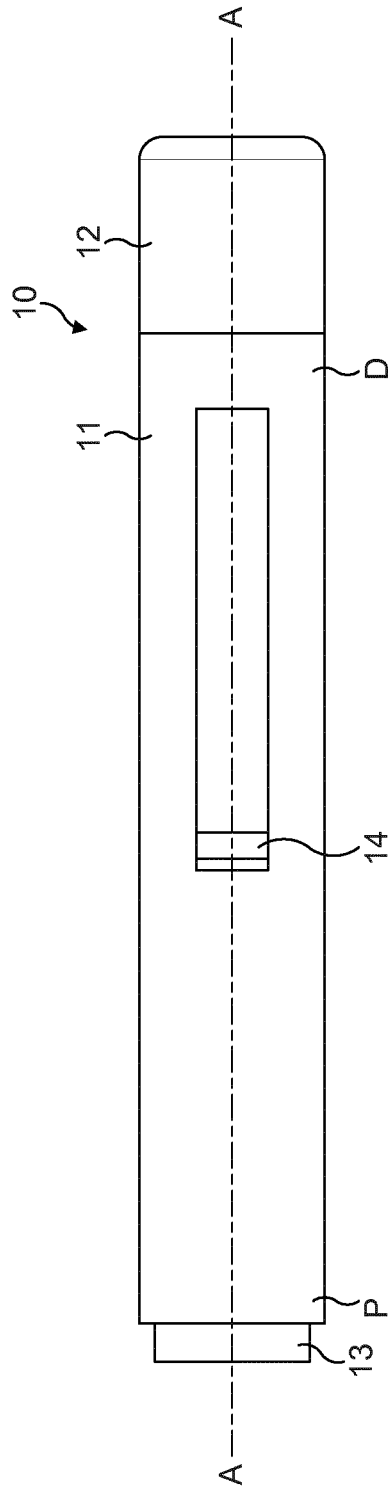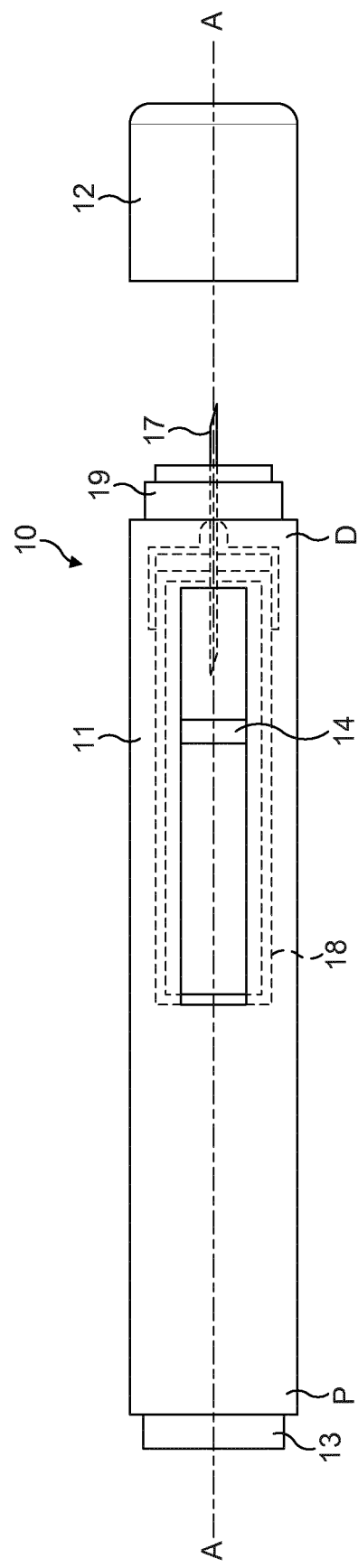
FIG. 1A
FIG. 1B

INJECTOR DEVICE

CROSS-REFERENCE TO RELATED APPLICATIONS

The present application is the national stage entry of International Patent Application No. PCT/EP2018/079548, filed on Oct. 29, 2018, and claims priority to Application No. EP 17306487.4, filed on Oct. 30, 2017, the disclosures of which are incorporated herein by reference.

TECHNICAL FIELD

The present disclosure relates to an injector device for a medicament.

BACKGROUND

Injection devices, for example auto-injectors, typically have a sealed container of medicament, and a needle for injection of the medicament into a patient. In one type of device, the medicament container may include a medicament cartridge and the needle may be initially separated from the cartridge. An initial action moves the cartridge and needle together so that the needle pierces the cartridge. In another type of device, the medicament container may include a syringe containing a medicament and the needle may be secured to the syringe. In both cases, a plunger or piston within the cartridge or syringe can be moved into the cartridge or syringe to dispense medicament through the needle for injection to a patient.

SUMMARY

In one aspect, an injector device includes an elongate housing having a proximal end and a distal end, and configured to receive container of medicament, a needle sleeve mounted within the housing and moveable between an extended position in which the needle sleeve at least partially extends from the distal end of the housing, and a retracted position in which the needle sleeve is received further within the housing than in the extended position, a piston rod moveable longitudinally within the housing, a piston spring configured to bias the piston rod towards a distal end of the housing to engage a container of medicament when received within the housing, and a release mechanism configured to control actuation of the piston rod, the release mechanism including a rotatable member disposed within the housing and in cooperating engagement with the needle sleeve such that movement of the needle sleeve from the extended position to the retracted position causes the rotatable member to rotate within the housing from a first position to a second position, at least one of the rotatable member and the needle sleeve including a helical guide track, the other of the rotatable member and the needle sleeve including a track follower in engagement with the helical guide track to rotate the rotatable member; wherein the rotatable member is in cooperating engagement with the piston rod by a guide track formed on one of the rotatable member and the piston rod, and a projection formed on the other of the rotatable member and the piston rod, the projection being received within the guide track, and the guide track being configured such that in the first position of the rotatable member, the piston rod is prevented from movement under the force of the piston spring, and in the second position of the rotatable member, the piston rod is free to move longitudinally within the housing under the force of the piston spring.

The rotatable member may have a first section of a first diameter and a second section of a second diameter, the longitudinal movement of the piston rod being from the second section towards the first section.

When the needle sleeve is in the extended position the rotatable member can be in the first position, when the needle sleeve has moved to the retracted position the rotatable member can be in the second position. The rotation of the rotatable member may be exclusively actuated by movement of the needle sleeve.

The guide track may include a first portion in which the projection is received when the rotatable member is in the first rotational position, and a second portion in which the projection is received when the rotatable member is in the second rotational position and when the piston rod moves longitudinally within the housing under the force of the piston spring. This may advantageously help provide two guide track portions which define locked and release positions of the release mechanism.

The first portion of the guide track may extend in a substantially circumferential direction of the rotatable member, and the second portion of the guide track extends in a substantially longitudinal direction of the rotatable member. This may advantageously help provide a locked position of the release mechanism until the rotatable member reaches a position for release of the piston rod.

The first portion of the guide track may extend in a helical path towards the second portion of the guide track. This may advantageously help reduce the force needed to rotate the rotatable member from the first to the second position of the rotatable member.

The first portion of the guide track may extend in a substantially perpendicular direction to the second portion of the guide track. This may advantageously help provide a secure locking position of the release mechanism against accidental activation under force of the piston spring.

The rotatable member may include a hollow cylindrical component and the piston rod may be disposed within the rotatable member, and the guide track may be formed on an inner surface of the rotatable member, and the projection may be formed on an outer surface of the piston rod. This may advantageously help provide a compact and space-efficient configuration of release mechanism.

The guide track may be a recessed groove in the rotatable member. This may advantageously help provide a compact rotatable member with reduced diameter. The guide track may alternatively be defined between spaced walls projecting from a surface of the rotatable member. This may advantageously help provide an alternative configuration of guide track without the need to machine or mould a groove, or may allow formation of a guide track on a rotatable member after manufacture of the rotatable member. Different configurations of guide track may thereby be produced.

The guide track may include a channel extending through a side wall of the rotatable member. This may advantageously help provide a reduced mass of rotatable member, for a lighter injector device. This may also, or alternatively advantageously help provide a simpler manufacturing process for the rotatable member as machining accuracy and tolerance of producing a groove of a constant depth around a circular body is not required.

The release mechanism may include a plurality of guide tracks formed on one of the rotatable member and the piston rod, and a plurality of projections formed on the other of the rotatable member and the piston rod and respectively received within the guide tracks. This may advantageously help provide a stable and even movement of the release mechanism and rotatable member.

The cooperating engagement between the needle sleeve and the rotatable member may include a second guide track formed on one of the rotatable member and the needle sleeve and a second projection formed on the other of the rotatable member and the needle sleeve, the second projection being received within the second guide track, and the guide track being configured in a helical path such that movement of the needle sleeve from the extended position to the retracted position causes the rotatable member to rotate within the housing from a first position to a second position. This may advantageously help provide a compact and space-efficient release mechanism, and allow smooth movement of the rotatable member, and control of the rotational angle relative to the movement of the needle sleeve.

There may be provided a plurality of second guide tracks formed on one of the rotatable member and the needle sleeve, and a plurality of second projections formed on the other of the rotatable member and the needle sleeve and respectively received within the second guide tracks. This may advantageously help provide a stable and even movement of the release mechanism and rotatable member.

The injector device may further include a needle unit at the distal end of the housing and including an injection needle held in a needle holder. The needle unit may include a needle retained within a holder. The needle unit may be fixedly secured within the housing, or maybe moveable within the housing. This may advantageously help provide a compact device of simple construction and ease of assembly. It may also advantageously help provide a device in which a needle can be pre-provided, and a medicament container later provided in a separate manufacturing or assembly step.

The rotatable member may rotate through around 90 degrees between the first position and the second position. This may advantageously help provide sufficient movement to provide distinct release and locking positions, but also not excessive rotation to be required to activate the release mechanism.

The injector device may further include a container of medicament received within the housing between the piston rod and the distal end of the injector device. The medicament container may include a cartridge of medicament, or may include a pre-filled syringe of medicament. The container of medicament may be moveable within the housing, or may be fixedly secured within the housing.

Also provided is a method of operating an injector device, the device including an elongate housing having a proximal end and a distal end and configured to receive a container of medicament, a needle sleeve mounted within the housing and moveable between an extended position in which the needle sleeve at least partially extends from the distal end of the housing, and a retracted position in which the needle sleeve is received further within the housing than in the extended position, a piston rod moveable longitudinally within the housing, a piston spring configured to bias the piston rod towards a distal end of the housing to engage a container of medicament when received within the housing, and a release mechanism configured to control actuation of the piston rod, the release mechanism including a rotatable member disposed within the housing and in cooperating engagement with the needle sleeve, and the rotatable member is in cooperating engagement with the piston rod by a guide track formed on one of the rotatable member and the piston rod, and a projection formed on the other of the rotatable member and the piston rod, the projection being received within the guide track, the method including moving the needle sleeve from the extended position to the retracted position and thereby causing the rotatable member to rotate within the housing from a first position in which the piston rod is prevented from movement under the force of the piston spring to a second position in which the piston rod is free to move longitudinally within the housing under the force of the piston spring.

These and other aspects of the disclosure will be apparent from and elucidated with reference to the embodiments described hereinafter.

BRIEF DESCRIPTION OF THE FIGURES

Embodiments will now be described, by way of example, with reference to the accompanying drawings.

FIG. 1A is a schematic side view of an injector device and a removable cap.

FIG. 1B is a schematic side view of the injector device of FIG. 1A, with the cap removed from the housing.

DETAILED DESCRIPTION

Figure 2:
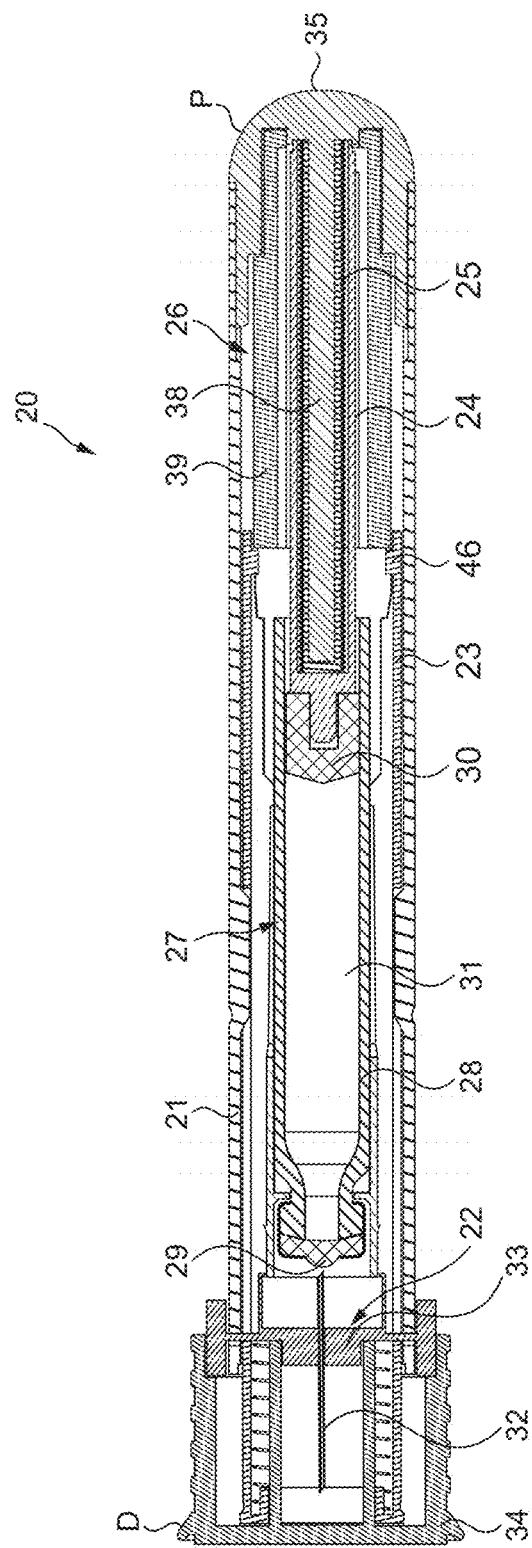
FIG. 2 is a side cross-sectional view of an injector device of a first embodiment.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of device, including an auto-injector. The device can include a cartridge-based system that requires piercing a sealed ampule before use. Volumes of medicament delivered with these various devices can range from about 0.5 ml to about 3 ml. Another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml). Yet another device may include a pre-filled syringe within a housing of the device. The syringe may be fixed within the housing or may be moveable within the housing, for example from a retracted position to an operation extended position.

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 17 and 29 Gauge.

The delivery devices described herein can also include one or more automated functions. For example, one or more of combining the needle and cartridge, needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include an actuator, for example, one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of combining the needle and cartridge, needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A and 1B. Device 10, as described above, is configured to inject a medicament into a patient's body. Device 10 includes a housing 11 which typically contains a cartridge or pre-filled syringe that defines a reservoir containing the medicament to be injected, and the components required to facilitate one or more steps of the delivery process.

The device 10 can also include a cap 12 that can be detachably mounted to the housing 11. Typically, a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of sleeve 19 relative to housing 11. For example, sleeve 19 can move in a longitudinal direction parallel to longitudinal axis A-A. Specifically, movement of sleeve 19 in a proximal direction can permit a needle 17 to extend from distal region D of housing 11.

Insertion of needle 17 can occur via several mechanisms. For example, needle 17 may be fixedly located relative to housing 11 and initially be located within an extended needle sleeve 19. Proximal movement of sleeve 19 by placing a distal end of sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 19.

Another form of insertion is "automated", whereby needle 17 moves relative to housing 11. Such insertion can be triggered by movement of sleeve 19. In other types of device, another form of activation may be provided, such as, for example, a button 13. As shown in FIGS. 1A and 1B, button 13 is located at a proximal end of housing 11. However, in other embodiments, button 13 could be located on a side of housing 11.

Other manual or automated features can include drug injection or needle retraction, or both. Injection is the process by which a bung or piston 14 is moved from a proximal location to a more distal location within the reservoir of the cartridge 18 in order to force a medicament from the cartridge 18 through needle 17. In some embodiments, a drive spring (not shown) is under compression before device 10 is activated. A proximal end of the drive spring can be fixed within proximal region P of housing 11, and a distal end of the drive spring can be configured to apply a compressive force to a proximal surface of piston 14. Following activation, at least part of the energy stored in the drive spring can be applied to the proximal surface of piston 14. This compressive force can act on piston 14 to move it in a distal direction. Such distal movement acts to compress the liquid medicament within the cartridge 18, forcing it out of needle 17.

Following injection, needle 17 can be retracted within sleeve 19 or housing 11. Retraction can occur when sleeve 19 moves distally as a user removes device 10 from a patient's body. This can occur as needle 17 remains fixedly located relative to housing 11. Once a distal end of sleeve 19 has moved past a distal end of needle 17, and needle 17 is covered, sleeve 19 can be locked. Such locking can include locking any proximal movement of sleeve 19 relative to housing 11.

Another form of needle retraction can occur if needle 17 is moved relative to housing 11. Such movement can occur if the cartridge 18 within housing 11 is moved in a proximal direction relative to housing 11. This proximal movement can be achieved by using a retraction spring (not shown), located in distal region D. A compressed retraction spring, when activated, can supply sufficient force to the cartridge 18 to move it in a proximal direction. Following sufficient retraction, any relative movement between needle 17 and housing 11 can be locked with a locking mechanism. In addition, button 13 or other components of device 10 can be locked as required.

FIG. 2 shows an injector device 20 of a first embodiment, including a housing 21, a needle unit 22, a needle sleeve 23, a piston rod 24, a piston spring 25, and a release mechanism 26. The piston rod 24 is configured to move within the housing 21 in a longitudinal direction of the injector device 20. The piston rod 24 is prevented from rotational movement within the housing by appropriate co-operating features (not shown) on the piston rod 24 and either the housing 21 or a rear cap 35 at an end of the housing 21.

The injector device 20 includes a distal end D and a proximal end P. The term "distal" refers to a location that is relatively closer to a site of injection, and the term "proximal" refers to a location that is relatively further away from the injection site. References hereinafter to "distal" and "proximal" are made in reference to the distal and proximal ends D, P respectively of the injector device 20. The housing 21 is configured to contain a medicament cartridge 27, as shown in FIG. 2. Such a medicament cartridge 27 includes a cylindrical container 28 having a distal end which is sealed with a pierceable seal 29 and a proximal end which is sealed with a piston 30 disposed within the proximal end of the container 28. Medicament 31 is held within the container 28 between the piercable seal 29 and the piston 30.

The needle unit 22 includes a needle 32 held in a needle holder 33 connected to the distal end of the housing 21. The needle sleeve 23 is connected to the housing 21 and configured to slide within the housing 21 in a longitudinal direction of the injector device 20. The needle sleeve 23 is moveable between an extended position and a retracted position. In the extended position, the needle sleeve 23 surrounds and shields the needle 32. In the retracted position, the needle 32 is exposed beyond the end of the needle sleeve 23. The needle sleeve 23 is shown in the extended position in FIG. 2. Also shown in FIG. 2 is an end cap 34 that initially covers the end of the needle sleeve 23 before use of the injector device 20.

Figure 4:
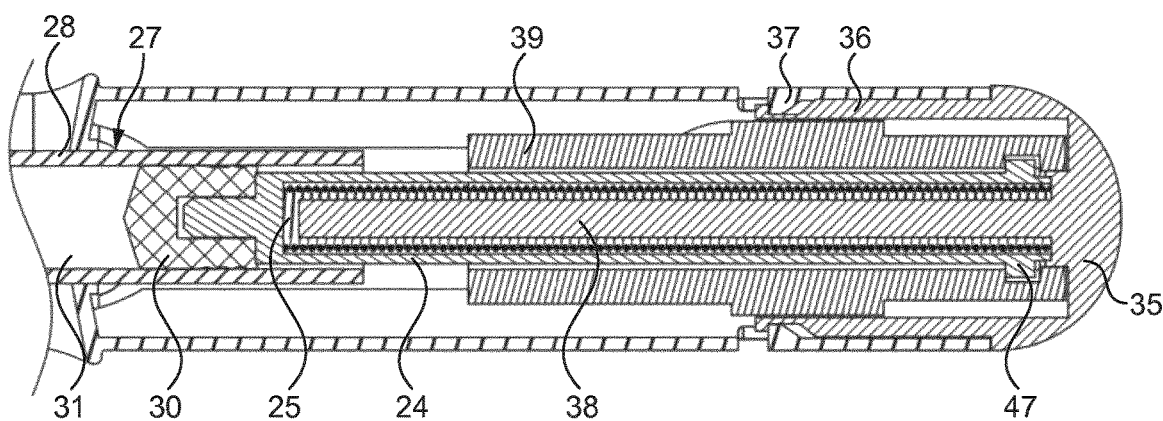
FIG. 4 is an enlarged cross-sectional view of the proximal end of the injector device of FIG. 2 illustrating the release mechanism in the starting position but taken with the injector device rotated through 90 degrees about its longitudinal axis from the position shown in FIG. 3.

The proximal end of the injector device 20 includes the rear cap 35 which is retained in place by locking arms 36 which engage with corresponding locking portions 37 formed on the housing 21 (see FIG. 4).

The piston spring 25 is disposed around an elongate projection 38 extending from the rear cap 35. The piston rod 24 has a hollow bore and is disposed over the elongate projection 38 and piston spring 25 such that the elongate projection 38 and piston spring 25 are received within the hollow bore of the piston rod 24. The piston spring 25 is in contact with the rear cap and urges the piston rod 24 in a distal direction of the injector device 20. When a medicament cartridge 27 is received within the injector device, the piston rod 24 is in contact with the piston 30 and is configured to drive the piston 30 within the container 28 once the piston rod 24 is released.

Figure 3:
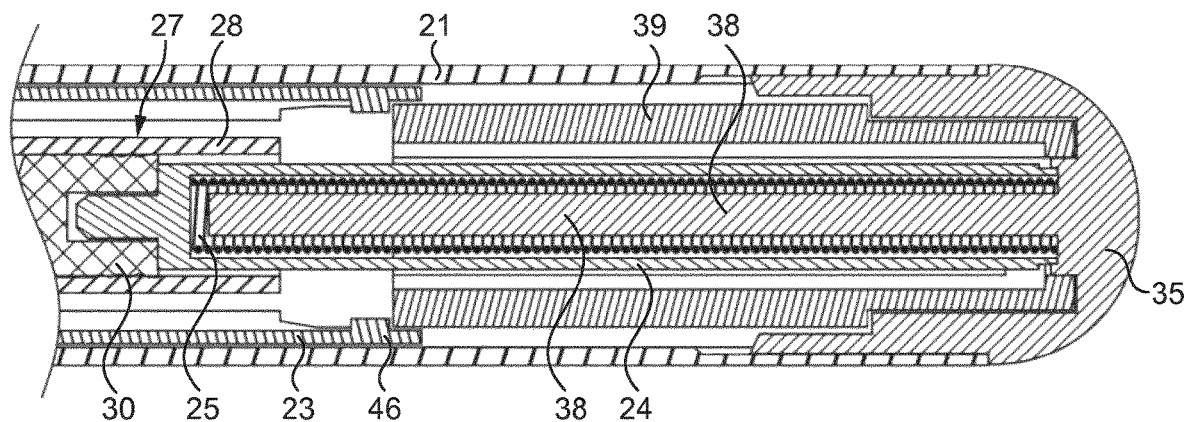
FIG. 3 is an enlarged cross-sectional view of a proximal end of the injector device of FIG. 2 illustrating the release mechanism in a starting position.
Figure 5:
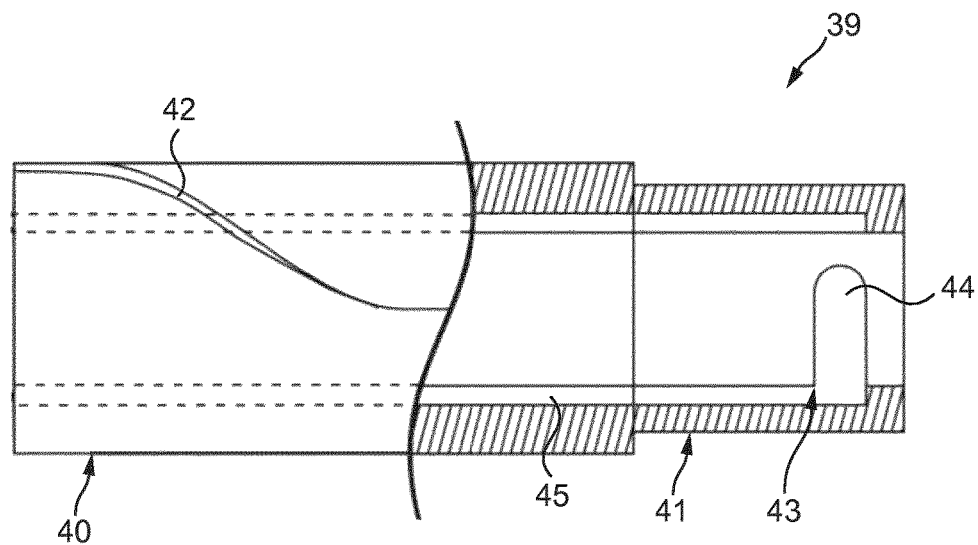
FIG. 5 is a side partial cross-sectional view of a rotator of the release mechanism of the injector device shown in FIGS. 2 to 4.
Figure 6:
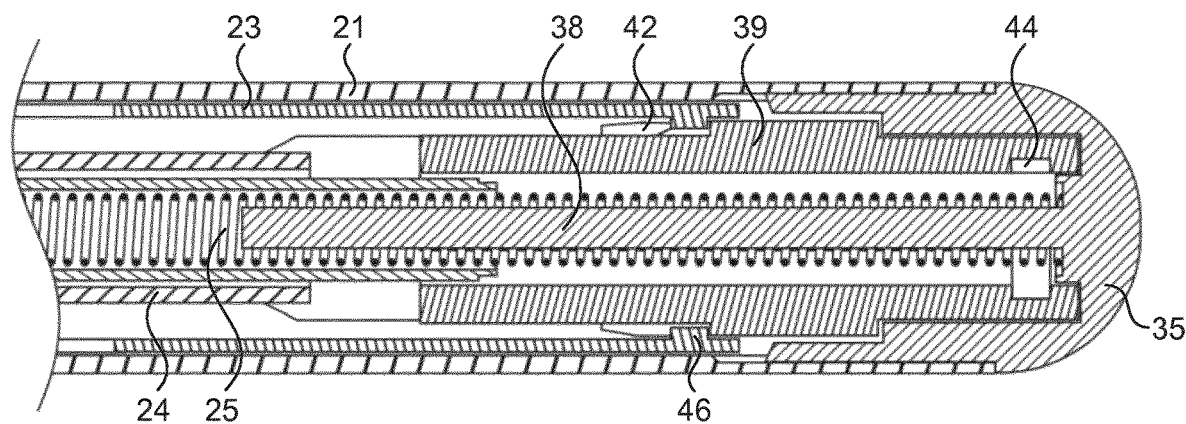
FIG. 6 is an enlarged cross-sectional view of the proximal end of the injector device of FIG. 2 and taken along the same section as FIG. 3 but illustrating the release mechanism during an injection process.
Figure 7:
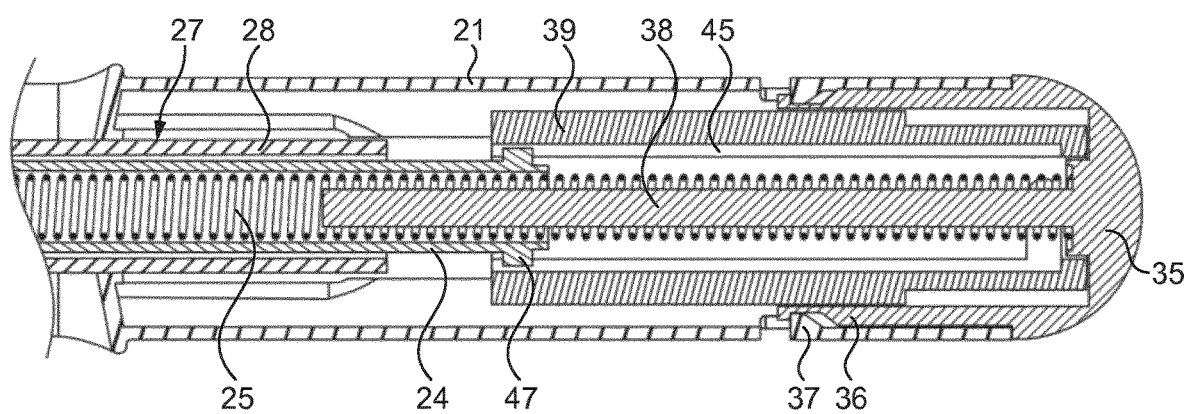
FIG. 7 is an enlarged cross-sectional view of the proximal end of the injector device of FIG. 2 illustrating the release mechanism during an injection process but taken with the injector device rotated through 90 degrees about its longitudinal axis from the position shown in FIG. 6.

The release mechanism 26 can be seen in more detail in FIGS. 3 and 4, which show the injector device 20 in an initial, starting position, before a medicament delivery process is commenced, and also with reference to FIG. 5. The release mechanism 26 includes a rotatable element 39 (hereinafter referred to as "rotator" for brevity) which is in cooperating engagement with the needle sleeve 23 and piston rod 24 in the starting position, as described hereafter. The rotator 39 is shown in isolation in FIG. 5. The rotator 39 is moveably mounted within the housing 21 so as to be able to rotate within the housing 21 about a longitudinal axis of the housing 21. The rotator 39 includes a hollow cylindrical component having a first section 40 of a first diameter and a second section 41 of a second diameter which is less than the first diameter. The rotator 39 includes an outer guide track 42 including a recessed channel formed in an outer surface of the first section 40. The outer guide track 42 is formed in a helical path and spirals around the outer surface of the first section. The outer guide track 42 is open at the distal end of the first section 40 of the rotator 39. In the exemplary embodiment shown, the outer guide track 42 extends around 90 degrees of the circumference of the rotator 39.

The rotator 39 further includes an inner guide track 43 including a recessed channel formed in an inner surface of the first and second sections 40, 41. The inner guide track 43 includes a first portion 44 which extends around a portion of the inner circumference of the inner surface of the second section 41 of the rotator 39. In the exemplary embodiment shown, the first portion 44 of the inner guide track 43 extends around 90 degrees of the inner circumference of the rotator 39. The inner guide track 43 also includes a second portion 45 which extends longitudinally along the inner surface of the second section 41 of the rotator 39, but does not extend circumferentially around the inner surface of the rotator 39. The first and second portions 44, 45 are connected at a right-angle, and the opposite end of the second portion 45 is open at a remote end of the first section of the rotator 39 that is distal to the second section 41.

The release mechanism 26 further includes a first pin 46 projecting inwardly from an inner face of the needle sleeve 23. The first pin 46 is configured to be received in the outer guide track 42. The release mechanism 26 further includes a second pin 47 projecting outwardly from an outer face of the piston rod 24 proximate a proximal end of the piston rod 24. The second pin 47 is received in the inner guide track 43. In the starting position shown in FIGS. 3 and 4, the second pin 47 is disposed at the end of the first portion 44 of the inner guide track 43 remote from the second portion 45. Although the rotator 39 is rotatable within the housing 21, it cannot move longitudinally in an axial direction of the housing. Longitudinal movement of the rotator 39 within the housing 21 is prevented by cooperating features (not shown) on the rotator 39 and either the end cap 35 or housing 21.

The second pin 47 being located within the first portion 44 of the inner guide track 43 thereby prevents the piston rod 24 from moving towards the distal end D of the injector device 20 under the force of the piston spring 25.

Operation of the injector device 20 of the first embodiment will now be described. The injector device 20 is initially in the starting position in which the release mechanism 26 is configured as shown in FIGS. 3 and 4. The first pin 46 on the needle sleeve 23 is disposed distal to the end of the first section 41 of the rotator 39 and axially aligned with the open end of the outer guide track 42 at the distal end of the first section 40 of the rotator 39. The second pin 47 disposed at the end of the first portion 44 of the inner guide track 43 remote from the second portion 45.

A user first removes the end cap 34 and then places the end of the needle sleeve against the intended injection site on the patient's skin. The user then presses the injector device 20 towards the patient's skin which causes the needle sleeve 23 to move into the housing 21 from its extended position to its retracted position. As needle sleeve 23 retracts into the housing 21, it engages the needle unit 22 so that the needle unit 22 moves in the proximal direction with the needle sleeve 23 such that the needle 32 engages and pierces the pierceable seal 29 of the cartridge 27. Further movement of the needle sleeve 23 into the housing 21 results in the needle unit 22 disengaging from the needle sleeve 23 such that the injection needle 32 is exposed and pierces the patient's skin in order for medicament to be delivered to the patient through the needle 32. Also as the needle sleeve 23 retracts into the housing, the first pin 46 on the needle sleeve 23 enters and travels along the outer guide track 42 of the rotator 39. Since the outer guide track 42 defines a helical path around the outside of the rotator 39, and the needle sleeve 23 moves linearly into the housing 21 without rotating, the rotator 39 is caused to rotate about the longitudinal axis of the injector device 20 within the housing 21. The rotator 39 rotates relative to the piston rod 24, and so the second pin 47 on the piston rod 24 is caused to move along the first portion 44 of the inner guide track 43. When the second pin 47 reaches the second portion 45 of the inner guide track 43, the piston rod 24 is then in a release position and is free to travel in a distal direction of the injector device 20 under the biasing force of the piston spring 25. During such movement, the second pin 47 travels longitudinally along the straight second portion 45 of the inner guide track 43.

As the piston rod 24 moves under the force of the piston spring 24, it pushes against the piston 30 of the medicament cartridge 27. It can be seen from FIG. 2 that in an initial configuration, before use, the needle unit 22 and medicament cartridge 27 are disposed within the housing 21 such that the needle 32 is spaced from the pierceable seal 29. As described above, in one embodiment, initial movement of the needle sleeve 23 causes the needle 32 to pierce the pierceable seal 29 before an injection procedure commences. Alternatively, however, as the medicament cartridge 27 is initially sealed by the pierceable seal 29 and the piston 30, the piston 30 cannot be pushed into the cylindrical container 28 and so the piston rod 24 may push the whole medicament cartridge 27 towards the needle unit 22, which may be fixed within the housing 21, until the needle 32 engages and pierces the pierceable seal 29. The distal end of the medicament cartridge then abuts the needle unit 22 and so cannot move further in the distal direction of the injector device 20. Thereafter, the piston rod 24 pushes the piston 30 into the cylindrical container 28 to cause the medicament 31 to be delivered into the patient's skin through the needle 32.

In a further alternative embodiment, as needle sleeve 23 retracts into the housing 21, it engages the needle unit 22 so that the needle unit 22 moves in the proximal direction with the needle sleeve 23 such that the needle 32 engages and pierces the pierceable seal 29 of the cartridge 27. Activation of the release mechanism 26 as described above may occur as the needle unit 22 engages the medicament cartridge 27, or may occur by further movement of the needle sleeve 23 into the housing 21 after the needle unit 22 disengages from the needle sleeve 23. However, the needle 32 may not yet pierce the patient's skin through movement of the needle sleeve 23 into the housing. Once the release mechanism 26 is activated as described above, the piston rod 24 may move under the force of the piston spring 24, pushing against the piston 30 of the medicament cartridge 27 such that the whole medicament cartridge 27 with engaged needle unit 22 is moved in the distal direction such that the needle 32 pierces the patient's skin and then the piston rod 24 pushes the piston 30 into the cylindrical container 28 to cause the medicament 31 to be delivered into the patient's skin through the needle 32.

In a further alternative embodiment, the medicament cartridge 27 may be fixedly secured within the housing 21. In such an embodiment, as needle sleeve 23 retracts into the housing 21, it engages the needle unit 22 so that the needle unit 22 moves in the proximal direction with the needle sleeve 23 such that the needle 32 engages and pierces the pierceable seal 29 of the cartridge 27. Further movement of the needle sleeve 23 into the housing 21 results in the needle unit 22 disengaging from the needle sleeve 23 such that the injection needle 32 is exposed and pierces the patient's skin in order for medicament to be delivered to the patient through the needle 32. Also as the needle sleeve 23 retracts into the housing, the release mechanism 26 is activated as described above. As the piston rod 24 moves under the force of the piston spring 25, it pushes against the piston 30 of the medicament cartridge 27 and pushes the piston 30 into the cylindrical container 28 to cause the medicament 31 to be delivered into the patient's skin through the needle 32.

Once the medicament delivery process is complete, the user moves the injector device away from the patient's skin and the needle 32 is withdrawn from the skin. The needle sleeve 23 then moves back into the extended position to surround and conceal the needle 32 to prevent the user accidentally injuring themselves on the needle 32. A locking mechanism (not shown) may be provided to lock the needle sleeve 23 in the extended position after use of the device.

Figure 8:
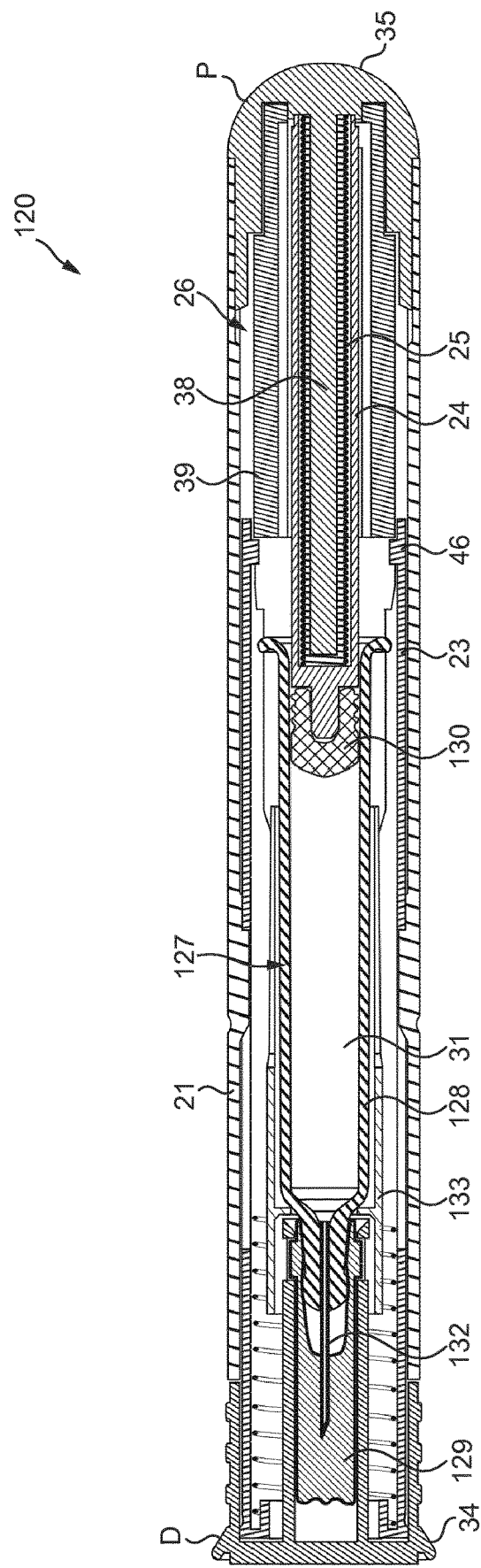
FIG. 8 is a side cross-sectional view of an injector device of a second embodiment, which includes a release mechanism as in the first embodiment, but wherein the injector device is configured to receive a pre-filled syringe.

FIG. 8 shows an injector device 120 of a second embodiment in which features in common with the injector device 20 of the first embodiment retain the same reference numerals and detailed description thereof will not be repeated. The injector device 120 of the second embodiment includes a housing 21, a needle sleeve 23, a piston rod 24, a piston spring 25, and a release mechanism 26 as described previously with respect to the injector device 20 of the first embodiment.

A difference with the injector device 120 of the second embodiment is that the housing 21 is configured to contain a different type of medicament container, namely a pre-filled syringe 127 instead of a medicament cartridge 27 as in the first embodiment. The pre-filled syringe includes a cylindrical body 128 having a distal end which a needle 132 is fixed, and a proximal end which is sealed with a piston 130 disposed within the proximal end of the cylindrical body 128. Medicament 31 is held within the cylindrical body 128 between the needle 132 and the piston 130. The pre-filled syringe 127 is fixedly retained within the housing 21. In the exemplary embodiment shown, the pre-filled syringe is held in a syringe holder 133 within the housing 21.

A needle cap 129 is provided around the needle 132 and is in frictional engagement with a narrowed portion of the cylindrical body 128 at its distal end that retains the needle 132. The needle cap 129 is received within the end cap 34 and is secured to the end cap 34 such that removal of the end cap 34 causes the needle cap 129 to be separated from the cylindrical body 128. The needle cap 129 may be secured to the end cap 34 by frictional engagement or by bonding, or by being otherwise mechanically secured to the end cap 34.

As with the injector device 20 of the first embodiment, the needle sleeve 23 is configured to slide within the housing 21 between an extended position in which the needle sleeve 23 surrounds the needle 132 and a retracted position in which the needle 132 is exposed beyond the end of the needle sleeve 23. The needle sleeve 23 is shown in the extended position in FIG. 8.

The release mechanism 26 is as described previously with respect to the injector device 20 of the first embodiment and so will not be described again.

Operation of the injector device 120 of the second embodiment will now be described. The injector device 120 is initially in the starting position in which the release mechanism 26 is configured as shown in FIG. 8. The first pin 46 on the needle sleeve 23 is disposed distal to the end of the first section 41 of the rotator 39 and axially aligned with the open end of the outer guide track 42 at the distal end of the first section 40 of the rotator 39. The second pin 47 is disposed at the end of the first portion 44 of the inner guide track 43 remote from the second portion 45.

A user first removes the end cap 34 and with it the needle cap 129, and then places the end of the needle sleeve 23 against the intended injection site on the patient's skin. The user then presses the injector device 20 towards the patient's skin which causes the needle sleeve 23 to move into the housing 21 from its extended position to its retracted position. As needle sleeve 23 retracts into the housing 21, the needle 132 is exposed and pierces the patient's skin. Also as the needle sleeve 23 retracts into the housing, the first pin 46 on the needle sleeve 23 enters and travels along the outer guide track 42 of the rotator 39. Since the outer guide track 42 defines a helical path around the outside of the rotator 39, and the needle sleeve 23 moves linearly into the housing 21 without rotating, the rotator 39 is caused to rotate about the longitudinal axis of the injector device 20 within the housing 21. The rotator 39 rotates relative to the piston rod 24, and so the second pin 47 on the piston rod 24 is caused to move along the first portion 44 of the inner guide track 43. When the second pin 47 reaches the second portion 45 of the inner guide track 43, the piston rod 24 is then in a release position and is free to travel in a distal direction of the injector device 20 under the biasing force of the piston spring 25. During such movement, the second pin 47 travels longitudinally along the straight second portion 45 of the inner guide track 43.

As the piston rod 24 moves under the force of the piston spring 24, it pushes against the piston 130 of the pre-filled syringe 127. Since the pre-filled syringe 127 is fixedly held within the housing 21, the piston rod 24 pushes the piston 130 into the cylindrical body 128 of the pre-filled syringe 127 to cause the medicament 31 to be delivered into the patient's skin through the needle 132.

Once the medicament delivery process is complete, the user moves the injector device 120 away from the patient's skin and the needle 132 is withdrawn from the skin. The needle sleeve 23 then moves back into the extended position to surround and conceal the needle 132 to prevent the user accidentally injuring themselves on the needle 132. A locking mechanism (not shown) may be provided to lock the needle sleeve 23 in the extended position after use of the device.

Although the above description and accompanying drawings describe injector devices 20, 120 of first and second embodiments, variations are envisaged. For example, although the outer guide track 42 is described as being formed on the rotator 39 and the first pin 46 is described as being formed on the needle sleeve 23, these features may be reversed such that the outer guide track 42 is formed on the needle sleeve 23 and the first pin 46 is formed on the rotator 39.

Similarly to the above, although the inner guide track 43 is described as being formed on the rotator 39 and the second pin 47 is described as being formed on the piston rod 24, these features may be reversed such that the inner guide track 43 is formed on the piston rod 24 and the second pin 47 is formed on the rotator 39.

In the embodiments described above, the outer and inner guide tracks are described as being recessed into the rotator 39 (or needle sleeve 23 or piston rod 24 respectively). However, in an alternative embodiment, the outer and/or the inner guide tracks may be defined by upstanding walls or ribs formed on the rotator 39, needle sleeve 23 or piston rod 24 respectively. Furthermore, in another alternative embodiment, the outer and/or the inner guide tracks may be defined by open slots extending entirely through the wall of the rotator 39, needle sleeve 23 or piston rod 24 respectively.

Although in the embodiments described above, one outer guide track 42 and one first projection 46 is described, two outer guide tracks 42 and two respective first projections 46 may be provided, or more generally a plurality of outer guide tracks 42 and a plurality of respective first projections 46 may be provided.

Similarly to the above, although in the embodiments described above, one inner guide track 43 and one second projection 47 is described, two inner guide tracks 43 and two respective second projections 47 may be provided, or more generally a plurality of inner guide tracks 43 and a plurality of respective second projections 47 may be provided. A plurality of outer/inner guide tracks and respective first/second projections may advantageously help towards providing more stable relative movement of the needle sleeve and rotator, and rotator and piston rod.

In the embodiments described above, the outer guide track advantageously extends around 90 degrees of the circumference of the rotator 39, although it is not limited to this angular value. In alternative embodiments, the outer guide track may extend around more or less than 90 degrees of the circumference of the rotator.

Similarly to the above, although the first portion 44 of the inner guide track 43 advantageously extends around 90 degrees of the circumference of the rotator 39, it is not limited to this angular value. In alternative embodiments, the first portion 44 of the inner guide track 43 may extend around more or less than 90 degrees of the circumference of the rotator 39.

In the embodiments described above, the first portion 44 of the inner guide track 43 extends circumferentially around the rotator 39, in a direction perpendicular to the longitudinal axis of the rotator 39. That is, the path of the first portion 44 of the inner guide track 43 does not extend in a longitudinal or axial direction of the rotator. However, it is not limited to this particular configuration of first portion 44 of the inner guide track 43. In alternative embodiments, the first portion 44 of the inner guide track 43 may be of a helical shape, formed with a shallow screw pitch such that the path of the first portion 44 of the inner guide track 43 extends in a longitudinal or axial direction of the rotator 39. This may advantageously help toward reducing the force necessary to rotate the rotator 39 as the piston spring 25 would help urge the piston 24 and associated second projections 47 along the first portion 44 of the inner guide track 43. However, it is important that the first portion 44 of the inner guide track 43 is self-locking with respect to the piston rod 24. That is, the pitch of the first portion 44 of the inner guide track 43 must not be large enough that the piston rod 24, under the force of the piston spring 25, can rotate the rotator 39 and automatically release the piston rod 24.

The first and second embodiments of injector devices described herein respectively are configured to receive a cartridge of medicament and a syringe pre-filled with a medicament. Herein, the term "medicament container" is intended to encompass both a cartridge of medicament and a pre-filled syringe.

Although in the embodiments described above, the particular term "pin" is used to describe the first and second pins 46, 47 that are received in the outer and inner guide tracks 42, 43 respectively, this is exemplary terminology and such features may be termed differently, and are more generally projecting elements which serve as followers in the respective guide tracks.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injector device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injector devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin.

Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not include a full-length antibody polypeptide, but that still includes at least a portion of a full-length antibody polypeptide that is capable of binding to an antigen. Antibody fragments can include a cleaved portion of a full length antibody polypeptide, although the term is not limited to such cleaved fragments. Antibody fragments include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL6 mAb (e.g., Sarilumab), and anti IL-4 mAb (e.g., Dupilumab).

The compounds described herein may be used in pharmaceutical formulations including (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

The invention claimed is:

1. An injector device comprising:
an elongate housing having a proximal end and a distal end, and configured to receive a container of medicament;
a needle sleeve mounted within the elongate housing and moveable between an extended position in which the needle sleeve at least partially extends from the distal end of the elongate housing, and a retracted position in which the needle sleeve is received further within the elongate housing than in the extended position;
a piston rod moveable longitudinally within the elongate housing;
a piston spring configured to bias the piston rod towards the distal end of the elongate housing to engage the container of medicament when received within the elongate housing; and
a release mechanism configured to control actuation of the piston rod, the release mechanism comprising a rotatable member disposed within the elongate housing and in cooperating engagement with the needle sleeve such that movement of the needle sleeve from the extended position to the retracted position causes the rotatable member to rotate within the elongate housing from a first position to a second position, at least one of the rotatable member and the needle sleeve comprising a first guide track extending around at least 90 degrees of a circumference of the rotatable member and at least a portion of the first guide track having a helical or spiral shape, the other of the rotatable member and the needle sleeve comprising a track follower in engagement with the first guide track to rotate the rotatable member;
wherein the rotatable member is in cooperating engagement with the piston rod by a second guide track formed on one of the rotatable member and the piston rod, and a projection formed on the other of the rotatable member and the piston rod, the projection being received within the second guide track, and the second guide track being configured such that in the first position of the rotatable member, the piston rod is prevented from movement under a force of the piston spring, and in the second position of the rotatable member, the piston rod is free to move longitudinally within the elongate housing under the force of the piston spring.

2. The injector device according to claim 1, wherein the rotatable member has a first section of a first diameter and a second section of a second diameter, the first section being distal of second section.

3. The injector device according to claim 1, wherein when the needle sleeve is in the extended position the rotatable member is in the first position, when the needle sleeve has moved to the retracted position the rotatable member is in the second position, and the rotation of the rotatable member is exclusively actuated by movement of the needle sleeve.

4. The injector device according to claim 1, wherein the second guide track comprises a first portion in which the projection is received when the rotatable member is in the first position, and a second portion in which the projection is received when the rotatable member is in the second position and when the piston rod moves longitudinally within the elongate housing under the force of the piston spring.

5. The injector device according to claim 4, wherein the first portion of the second guide track extends in a substantially circumferential direction of the rotatable member, and the second portion of the second guide track extends in a substantially longitudinal direction of the rotatable member.

6. The injector device according to claim 5, wherein the first portion of the second guide track extends in a helical path towards the second portion of the second guide track.

7. The injector device according to claim 4, wherein the first portion of the second guide track extends in a substantially perpendicular direction to the second portion of the second guide track.

8. The injector device according to claim 1, wherein the rotatable member comprises a hollow cylindrical component, the piston rod is disposed within the rotatable member, the second guide track is formed on an inner surface of the rotatable member, and the projection is formed on an outer surface of the piston rod.

9. The injector device according to claim 1, wherein the second guide track is defined between spaced walls projecting from a surface of the rotatable member.

10. The injector device according to claim 1, wherein the second guide track comprises a recessed channel formed in a surface of the rotatable member, or the second guide track comprises a channel extending through a side wall of the rotatable member.

11. The injector device according to claim 1, wherein the release mechanism comprises a plurality of guide tracks formed on one of the rotatable member and the piston rod, and a plurality of projections formed on the other of the rotatable member and the piston rod are respectively received within the plurality of guide tracks.

12. The injector device according to claim 1, wherein the cooperating engagement between the needle sleeve and the rotatable member comprises (i) an additional guide track formed on one of the rotatable member and the needle sleeve and (ii) an additional projection formed on the other of the rotatable member and the needle sleeve, the additional projection being received within the additional guide track, and the additional guide track being configured in a helical path such that movement of the needle sleeve from the extended position to the retracted position causes the rotatable member to rotate within the elongate housing from the first position to the second position.

13. The injector device according to claim 12, comprising a plurality of additional guide tracks formed on one of the rotatable member and the needle sleeve, and a plurality of additional projections formed on the other of the rotatable member and the needle sleeve are respectively received within the additional guide tracks.

14. The injector device according to claim 1, further comprising the container of medicament received within the elongate housing between the piston rod and the distal end of the injector device.

15. The injector device according to claim 1, wherein a sidewall of the first guide track comprises a curved portion.

16. A method comprising:
moving a needle sleeve within an elongate housing of an injector device from an extended position in which the needle sleeve at least partially extends from a distal end of the elongate housing to a retracted position in which the needle sleeve is received further within the elongate housing than in the extended position;
receiving a track follower within a first guide track, the first guide track extending around at least 90 degrees of a circumference of a rotatable member and at least a portion of the first guide track having a helical or spiral shape, wherein the first guide track is formed on one of the rotatable member and the needle sleeve, and the track follower is formed on the other of the rotatable member and the needle sleeve, the rotatable member being part of a release mechanism of the injector device;
rotating the rotatable member within the elongate housing from a first position to a second position as the needle sleeve is moved from the extended position to the retracted position;
receiving a projection within a second guide track, wherein the second guide track is formed on one of the rotatable member and a piston rod, and the projection is formed on the other of the rotatable member and the piston rod; and
moving the piston rod distally within the elongate housing, by a piston spring, to engage a container of medicament received within the elongate housing upon rotating the rotatable member to the second position, wherein the movement of the piston rod is prevented when the rotatable member is in the first position and the movement of the piston rod is permitted when the rotatable member is in the second position.

17. The method of claim 16, further comprising preventing movement of the piston rod, when the rotatable member is in the first position, by the projection being located within a first portion of the second guide track.

18. The method of claim 16, further comprising:
piercing an injection needle into a pierceable septum of the container disposed within the elongate housing, wherein the injection needle is disposed at the distal end of the elongate housing; and
expelling medicament from the container under an action of the piston rod.

19. The method of claim 16, further comprising moving the track follower along the first guide track.

20. The method of claim 16, further comprising moving the projection along the second guide track, wherein a first portion of the second guide track extends in a substantially circumferential direction of the rotatable member, and a second portion of the second guide track extends in a substantially longitudinal direction of the rotatable member.

21. The method of claim 16, wherein the second guide track comprises a first portion in which the projection is received when the rotatable member is in the first position, and a second portion in which the projection is received when the rotatable member is in the second position and when the piston rod moves longitudinally within the elongate housing under a force of the piston spring.

* * * * *